United States Patent
Vrlijc et al.

(10) Patent No.: US 6,858,406 B1
(45) Date of Patent: Feb. 22, 2005

(54) PROCESS FOR THE MICROBIAL PRODUCTION OF AMINO ACIDS BY BOOSTED ACTIVITY OF EXPORT CARRIERS

(75) Inventors: Marina Vrlijc, Jülich (DE); Lothar Eggeling, Jülich (DE); Hermann Sahm, Jülich (DE)

(73) Assignee: Forschungszentrum Jülich GmbH, Jülich (DE)

( * ) Notice: Subject to any disclaimer, the term of this patent is extended or adjusted under 35 U.S.C. 154(b) by 0 days.

(21) Appl. No.: 09/105,117

(22) Filed: Jun. 17, 1998

Related U.S. Application Data (63) Continuation-in-part of application No. PCT/DE96/02485, filed on Dec. 18, 1996.

(30) Foreign Application Priority Data

Dec. 22, 1995 (DE) .......................... 195 48 222

(51) Int. Cl.⁷ ............................ C12P 21/06; C12N 1/20; C12N 5/00; C07H 21/04; C07K 14/00
(52) U.S. Cl. .............................. 435/69.1; 435/252.32; 435/325; 435/320.1; 435/252.3; 536/23.7; 536/24.1; 530/350
(58) Field of Search .......................... 435/69.1, 252.32, 435/325, 320.1, 252.3, 106, 252.1; 536/23.7, 24.1; 530/350

(56) References Cited

PUBLICATIONS

Lodish et al. "Molecular Cell Biology", Fourth edition, Publisher: W.H. Freeman & company, pp. 255–256, 1999.*
Vrljic et al. "Unbalance of L–Lysine flux in *Corynebacterium glutamicum* and its use for the isolation of excretion-–defective mutants", J. of Bacteriology, vol. 177 (4), Jul. 1995.*
Vrljic et al., "A new type of transporter with a new type of cellular function: L–lysine export from *Corynebacterium glutamicum*", 1996, Molecular Microbiology, vol. 22(5), pp. 815–826.*
Ayala et al., "Modern Genetics", second edition, 1984, Glossary.*

* cited by examiner

*Primary Examiner*—Karen Cochrane Carlson
*Assistant Examiner*—Rita Mitra
(74) *Attorney, Agent, or Firm*—Klaus J. Bach (57) ABSTRACT

The invention pertains to a process for the microbial production of amino acids. The process involves boosting the export carrier activity and/or export gene expression of a microorganism which produces the desired amino acid. It was found that a single specific gene is responsible for the export of a given amino acid, and on that basis, a process for the microbial production of amino acids, involving the controlled boosting of the export gene expression and/or export carrier activity of a microorganism was developed, which produces the amino acid. The boosted expression or activity of the export carrier resulting from this process increases the secretion rate and thus increases transport of the desired amino acid.

17 Claims, 4 Drawing Sheets

FIG.1

```
CgLysE    1 MVIMEIFITGLLLGASLLLSIGPQNVLVIKQGIKREGLIAVLLVCLISDV  50
            ::|.:||||.:|:.|||:|:   |  :  |:| |||:
EcYgga    1 ...............MILPLGPQNAFVMNQGIRRQYHIMIALLCAISDL  34

CgLysE   51 FLFIAGTLGVDLLSNAAPIVLDIMRWGGIAYLLWFAVMAAKDAMTNKVEA 100
            .|:.||.:|..  |  ..|  :|.::  |||:|:|||::.  |  |.||...:|
EcYgga   35 VLICAGIFGGSALLMQSPWLLALVTWGGVAFLLWYGFGAFKTAMSSNIE.  83

CgLysE  101 PQIIEETEPTVPDDTPLGGSAVATDTRNRVRVEVSVDKQRVWVKPMLMAI 150
            |::..| .:.|  :                              : :  ::|:
EcYgga   84 ...............LASAEVMKQGRWK............IIATMLAV 104

CgLysE  151 VLTWLNPNAYLDAFVFIGGVGAQYGDTGRWIFAAGAFAASLIWFPLVGFG 200
            |||||:.|||.||.:|::|:|.:     ..::  ||  |.:.||::||      :::
EcYgga  105 ..TWLNPHVYLDTFVVLGSLGGQLDVEPKRWFALGTISASFLWFFGLALL 152

CgLysE  201 AAALSRPLSSPKVWRWINVVVAVVMTALAIKLMLMG.........     236
            ||  |...|..:|. |  ||:||:.||   :|:.|     |
EcYgga  153 AAWLAPRLRTAKAQRIINLVVGCVMWFIALQLARDGIAHAQALFS 197
```

PROCESS FOR THE MICROBIAL PRODUCTION OF AMINO ACIDS BY BOOSTED ACTIVITY OF EXPORT CARRIERS

This application is a continuation in part of PCT/DE96/02485 filed on Dec. 18, 1996, which claims benefit of a foreign (German) application 195 48 222.0 filed on Dec. 22, 1995.

BACKGROUND OF THE INVENTION

The invention relates to a process for the microbial production of amino acids, to export genes, to regulator genes, to vectors, to transformed cells, to membrane proteins, and to uses.

Amino acids are of high economical interest and there are many applications for the amino acids: for example, L-lysine as well as L-threonine and L-tryptophan are needed as feed additives, L-glutamate as seasoning additive, L-isoleucine, and L-tryosine in the pharmaceutical industry, L-arginine and L-isoleucine as medicine or L-glutamate and L-phenylalanine as a starting substance for the synthesis of fine chemicals.

A preferred method for the manufacture of these different amino acids is the biotechnological manufacture by means of micro-organisms; since, in this way, the biologically effective and optically active form of the respective amino acid is directly obtained and simple and inexpensive raw materials can be used. As microorganisms, for example, *Corynebacterium glutamicum* and its relatives ssp. flavum and ssp lactofermentum (Liebl et al; Int. J-System Bacteriol (1991) 41:255–260) as well as *Escherichia coli* and related bacteria can be used.

However, these bacteria produce the amino acids only in the amounts needed for their growth such that no excess amino acids are generated and are available. The reason for this is that in the cell the biosynthesis of the amino acids is controlled in various ways. As a result, different methods of increasing the formation of products by overcoming the control mechanisms are already known. In these processes, for example, amino acid analogs are utilized to render the control of the biosynthesis ineffective. A method is described, for example, wherein *Corynebacterium* strains are used which are resistant to L-tyrosine and L-phenylalanine analogs (JP 19037/1976 and 39517/1978). Also methods have been described in which bacteria resistant to L-lysine and also to L-threonine analogs are used in order to overcome the control mechanisms (EP 0 205 849 B1, UK patent application GB 2 152 509 A).

Furthermore, microorganisms constructed by recombinant DNA techniques are known wherein the control of the biosynthesis has also been eliminated by cloning and expressing the genes which code for the key enzymes which cannot be feed-back inhibited any more. For example, a recombinant L-lysinee producing bacterium with plasmid-coded feedback-resistant aspartate kinase is known (EP 0381527). Also, a recombinant L-phenylalanine producing bacterium with feedback resistant prephenate dehyrodgenase has been described (JP 124375/1986; EP 0 488 424). In addition, increased amino acid yields have been obtained by overexpression of genes which do not code for feedback-sensitive enzymes of the amino acids synthesis. For example, the lysine formation is improved by increased synthesis of the dihydrodipicolinate synthase (EP 0 197 335). Also, the threonine formation is improved by increased synthesis of threonine dehydratase (EP 0 436 886 Al).

Further experiments for increasing the amino acid production aim at an improved generation of the cellular primary metabolites of the central metabolism. In this connection, it is known that the overexpression of the transketolase achieved by recombinant techniques improve the product generation of L-tryptophan, L-tyrosine or L-phenalanine (EP 0 600 463 A2). Furthermore, the reduction of the phosphenol pyruvate carboxylase activity in *Corynebacterium* provides for an improvement in the generation of aromatic amino acids (EP 0 331 145).

All these attempts to increase the productivity have the aim to overcome the limitation of the cytosolic synthesis of the amino acids. However, as a further limitation basically also the export of the amino acids formed in the interior of a cell into the culture medium should be taken into consideration. As a result, it has been tried to improve this export and, consequently, the efficiency of the amino acid production. For example, the cell permeability of the *Corynebacterium* has been increased by biotin deficiency, detergence or penicillin treatment. However, these treatments were effective exclusively in the production of glutamate, whereas the synthesis of other amino acids could not be improved in this manner. Also, bacteria strains have been developed in which the activity of the secretion system is increased by chemical or physical mutations. In this way, for example, a *Corynebacterium glutamicum* strain has been obtained which has an improved secretion activity and is therefore especially suitable for the L-Lysine production. (DE 02 03 320).

Altogether, the attempts to increase the secretion of amino-acids formed within the cell have all in common that an increase efflux of amino acids on the basis of the selected non-directed and non-specific methods could be achieved only accidentally.

Solely in the German patent application No. 195 23 279.8-41, a process is described which provides for a well-defined increase of the secretion of amino acids formed internally in a cell by increasing the expression of genes coding for the import of amino acids. The understanding on which this process was based, that is, the cell utilizes import proteins for the export of amino acids as well as the fact that by nature microorganisms do not generate and release excess amino acids lets one assume that export genes or proteins specific for the amino acid transport do not exist, but that the amino acids are excreted by way of other export systems.

The export systems known so far export poisonous metal ions, toxic antibiotica and higher molecular toxins. These export systems are relatively complex in their structure. Generally, membrane proteins of the cytoplasmic membrane are involved which however cause only a partial reaction of the export so that presumably additional extra cytoplasmic support proteins are needed for the transport (Dink, T. et al., A family of large molecules across the outer membranes of gram-negative bacteria., J. Bacteriol. 1994, 176: 3825–3831). Furthermore, it is known that, with the sec-dependent export system for extra-cellular proteins, at least six different protein components are essential for the export. This state-of-the-art suggests that also the systems, which are responsible for the export of amino acids, but which are not known so far comprise several protein components or respectively, several genes are responsible for the export of amino acids. A hint in this direction could be the various mutants which are defective in the lysine export as described by Vrylic et al.,(J. Bacteriol (1995) 177:4021–4027).

SUMMARY OF THE INVENTION

It has now been found surprisingly that only a single specific gene is responsible for the export of amino acids so that, in accordance with the invention, for the first time a method for the microbial manufacture of amino acids is provided wherein clearly the export gene expression and/or the export carrier activity of a microorganism producing amino acids is increased. The increased export expression or respectively, activity of the export carrier resulting from this process leads to an increased secretion rate so that the export of the respective amino acid is increased. The microorganisms so modified also accumulate an increased part of the respective amino acid in the culture medium.

For an increase in the export carrier activity especially the endogenic activity of an amino acid producing microorganism is increased. An increase of the enzyme activity can be obtained for example by an increased substrate consumption achieved by changing the catalytic center or by eliminating the effects of enzyme inhibitors. An increased enzyme activity can also be caused by an increased enzyme synthesis for example by gene amplification or by eliminating factors which inhibit the enzyme biosynthesis. The endogene export activity is increased preferably by mutation of the endogenic export gene. Such mutations can be generated either in an uncontrolled manner in accordance with classic methods as for example by UV irradiation or by mutation causing chemicals or in a controlled manner by gene-technological methods such as deletion(s) insertion(s) and/or nucleotide exchange(s).

The export gene expression is increased by increasing the number of gene copies and/or by increasing regulatory factors which positively affect the export gene expression. For example, a strengthening of regulatory elements takes place preferably on the transcription level by increasing particularly the transcription signals. This can be accomplished for example in that, by changing the promoter sequence arranged before the structure gene, the effectiveness of the promoter is increased or by completely replacing the promoter by more effective promoters. An amplification of the transcription can also be achieved by accordingly influencing a regulator gene assigned to the export gene as will be explained further below. On the other hand, an amplification of the translation is also possible, for example, by improving the stability of the m-RNA.

To increase the number of gene copies the export gene is installed in a gene construct or, respectively, in a vector, preferably, a vector with a small number of copies. The gene construct includes regulatory gene sequences, which are specifically assigned to the export gene, preferably such sequences, which re-inforce the gene expression. The regulatory gene sequences comprise a nucleotide sequence which codes for the amino acid sequence SEQ ID No.(B)3 and given in table 1 or the allele variations thereof or, respectively, a nucleotide sequence 1421 to 2293 according to SEQ ID No. (B)1shown in table 2 or a DNA sequence which is effective essentially in the same manner.

Allele variations or, respectively, equally effective DNA sequences comprise particularly functional derivatives which can be obtained by deletion(s) insertion(s) and/or substitution(s of nucleotides of corresponding sequences, wherein however the regulator protein activity or function is retained or even increased. In this way, the effectiveness of the interaction of the regulatory protein to the DNA of the export gene to be regulated can be influenced by mutating the regulatory gene sequence such that the transcription is strengthened and, consequently, the gene expression is increased. In addition, also so-called enhancers may be assigned to the export gene as regulatory sequences whereby, via an improved correlation between RNA polymerase and DNA, also the export gene expression is increased.

For the insertion of the export gene into a gene construct, the gene is preferably isolated from a microorganism strain of the type *Corynebacterium* and, with the gene construct including the export gene, a microorganism strain, especially *Corynebacterium*, producing the respective amino acid is transformed. The isolation and transformation of the respective transport gene occurs according to the usual methods. If a transport gene is isolated and cloned from *Corynebacterium* then for example, the method of homologuous complementation of an export defective mutant is suitable (J.Bacteriol. (1995)177: 4021–4027). If a direct cloning of the structure gene is not possible vector sequences may first be inserted into the transport gene whereupon it is isolated by way of "plasmid rescue" in the form of inactive fragments. For the process according to the invention genes from the *C. glutamicum* ATCC 13032 or *C. glutamicum* ssp. flavum 14067 or also, *C. glutamicum* ssp. lacto fermentum ATCC 13869 are particularly suitable. The isolation of the genes and their invitro recombination with known vectors (Appl. Env. Microbial (1989)55: 684–688; Gene 102(1991)93–98) is followed by the transformation into the amino acid producing strains by electroporation (Liebl et al. (1989)FEMS Microbiol Lett. 65; 299–304) or conjugation (Schafer et al. (1990) J. Bacteriol. 172:1663–1666). For the transfer, preferably vectors with low numbers of copies are used. As host cells, preferably such amino acid producers are used which are deregulated in the synthesis of the respective amino acids and/or which have an increased availability of central metabolism metabolites.

After isolation, export genes with nucleotide sequences can be obtained which code for the amino acid sequences given in SEQ ID No.(A)2 and shown in table 3 or for their allele variations or, respectively, which include the nucleotide sequence of 1016 to 1726 according to SEQ ID No. (A) 1 and table 2 or a DNAy sequence which is effective essentially in the same way. Also here, allele variations or equally effective DNA sequences include particularly functional derivatives in the sense indicated above for the regulatory sequences. These export genes are preferably used in the process according to the invention.

One or several DNA sequences can be connected to the export gene with or without attached promoter or respectively, with or without associated regulator gene, so that the gene is included in a gene structure.

By cloning of export genes, plasmids or, respectively, vectors can be obtained which contain the export gene and which, as already mentioned, are suitable for the transformation of an amino acid producer. The cells obtained by transformation which are mainly transformed cells from *Corynebacterium*, contain the gene in reproducible form, that is, with additional copies on the chromosome wherein the gene copies are integrated at any point of the genome by homologous recombination and/or on a plasmid or respectively, vector.

A multitude of sequences is known which code for membrane proteins of unknown function. By providing in accordance with the invention export genes such as the export gene with the nucleotide sequence of nucleotide 1016 to 1726 in accordance with SEQ ID No. 1 and table 2 or respectively, the corresponding export proteins for example that with the amino acid sequence according to SEQ ID No. 2, it is now possible to identify by sequence comparison membrane proteins, whose function is the transport of amino acids. The export gene identified in this way can subsequently be used to improve the amino acid production in accordance with the process of the invention.

The membrane proteins known from the state-of-the-art generally include 12, some also only 4 transmembrane helices. However, it has now been found surprisingly that the membrane proteins responsible or suitable for the export of amino acids include 6 transmembrane helices (see for example, the amino acid sequence of an export protein listed in SEQ ID No. 2 and table 3, wherein the 6 transmembrane areas have been highlighted by underlining). Consequently, there is a new class of membrane proteins present, which has not yet been described.

EXAMPLES a) Cloning of an export gene and cloning of a regulator of *Corynebacterium glutamicum*.

Chromosomal DNA from *C. glutamicum* R127 (FEMS Microbiol lett. (1989)65:299–304) was isolated as described by Scharzer et al. (Bio/Technology (1990) 9:84–87). The DNA was then split with the restriction enzyme Sau3A and separated by saccharose gradient centrifugation as described in Sambrook et al. (Molecular cloning, A laboratory manual (1989) Cold Spring Harbour Laboratory Press). The various fractions were analyzed gel electrophoretically with respect to their size and the fraction with a fragment size of about 6–10 kb was used for the ligation with the vector pJCl. In addition, the vector pJCl was linearized with BamHI and dephosphorylized. Five ng thereof was ligated with 20 ng of the chromosomal 6–10 kb fragments. With the whole ligation preparation, the export defective mutant NA8 (J. Bacterol. (1995)177:4021–4027) was transformed by electroporation (FEMS Microbiol Lett(1989)65:299–304). The transformants were selected for LBHIS(PEMS Microbiol. Lett. (1989)65:299–304) with 15 μg kanamycin per ml. These transformants were subjected to extensive plasmid analyses in that 200 of the altogether 4500 clones obtained were individually cultivated and their plasmid content and size was determined. On average, about half of the kanamycin-resistant clones carried a recombinant plasmid with an insert of the average size of 8 kb. This provides for a probability of 0.96 for the presence of any gene of *C. glutamicum* in the established gene bank. The 4500 obtained transformants were all individually checked for renewed presence of lysinee secretion. For this purpose, the system described by Vrljic for the induction of the Llysinee excretion in *Corynebacterium glutamicum* was utilized (J. Bacteriol (1995) 177:4021–4027). For this purpose, so-called minimal-medium-indicator plates were prepared, which contained per liter 20 g $(NH_4)_2SO_4$, 5 g uric acid, 1 g $KH_2PO_4$, 1 g $K_2HPO_4$, 0.25 g $MgSO_4 \times 7H_2O$, 42 g morpholino propane sulfonic acid, 1 ml $CaCl_2$ (1 g/100 ml), 750 ml dest., 1 ml Cg trace salts, 1 ml biotin (20 μg/1001), pH7, 4% glucose, 1.8 mg protocatechuic acid, 1 mg $FeSO_4 \times 7$ $H_2O$, 1 mg $MnSO_4 \times H_2O$, 0.1 mg $ZnSO_4 \times 7$ $H_2O$, 0.02 mg $CuSO_4$, 0.002 mg $NiCl_2 \times 6$ $H_2O$, 20 g agar-agar, as well as $10^7$ cells/ml of the lysine-auxotrophene *C. glutamicum* mutant 49/3. The original 4500 transformants were all individually pinned, by toothpicks onto the indicator plates with, in each case, a check of the original non-excretor NAB (J.Bacteriol (1995)177:4021–4027) and the original strain R127. At the same time, always 2 plates were inoculated of which only one contained additionally SmM L-methionine in order to induce the lysine excretion in this way.

The indicator plates were incubated at 30° C. and examined after 15, 24 and 48 hours. In this way, altogether 29 clones were obtained which showed on the indicator plate provided with methionine a growth court by the indicator strain 49/3. The clones were examined individually and then again as described above, for reestablishment of the growth court. In this way, the two clones NA8 pMVB-5-24 and NA8 pMV6-3 were obtained which had again received the capability to excrete lysine.

Figure 1:
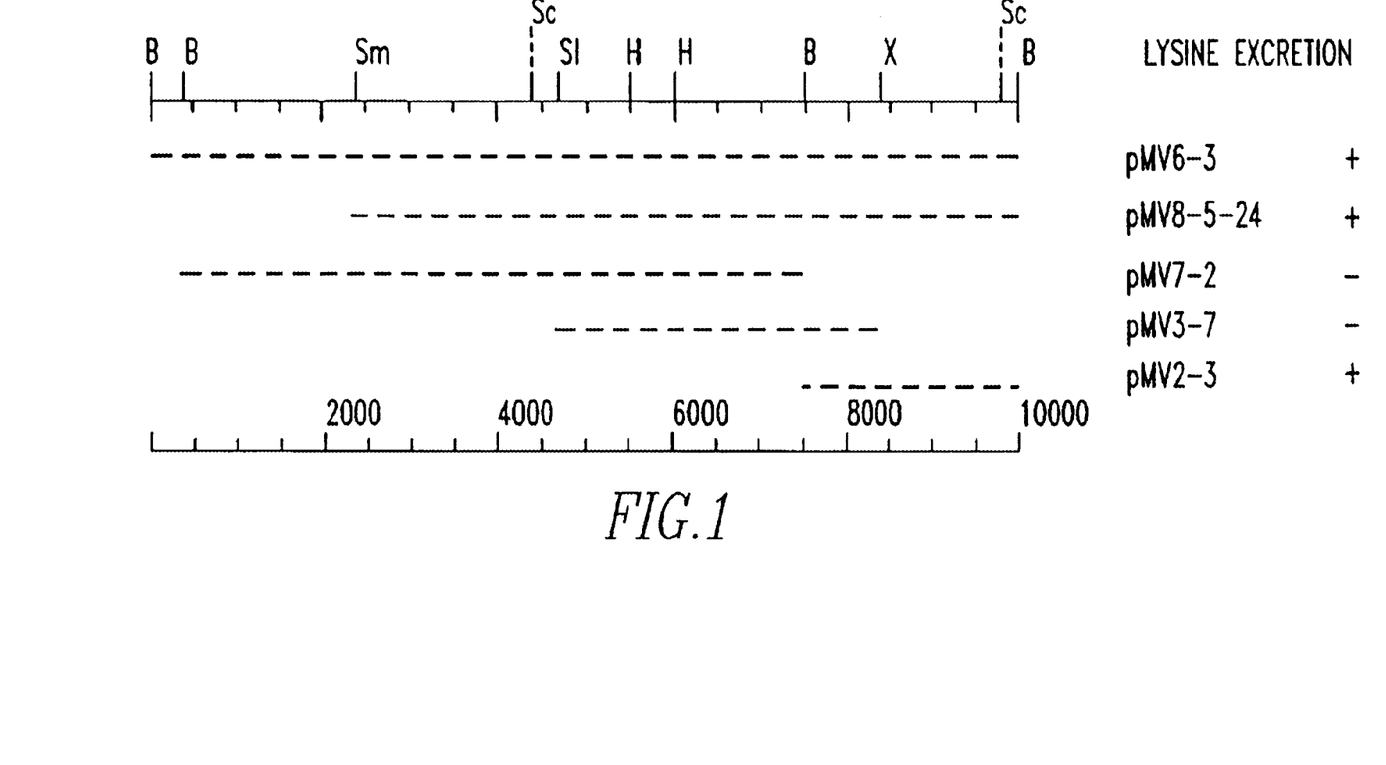
FIG. 1 shows the fragments in pMV6-3 and pMV8-5-24 obtained by the cloning which cause the lysine secretion and the subclone pMV2-3 made from pMV6-3, which also causes the lysine 30 secretion and which was sequenced. B₁BamHl; Sm, SmaI; Se, SacI; S1, Sal I,II, HindII; X, XhoI.

From these clones, plasmid preparations were performed as described in Schwarzer et al. (Bio/Technology (1990)9; 84–87). By retransformation in NA8, the plasmid-connected effect of the excretion of L-lysine was confirmed. Both plasmids were subjected to a restriction analysis. Plasmid pMVB-5-24 carries an insert of 8.3 kb, and pMV6-3 one of 9.5 kb. The physical charter of the inserts is shown in FIG. 1.

b) Subcloning of an DNA fragment which reconstitutes the lysine export.

From the insert of the plasmid pMV6-3 individual subclones were prepared utilizing the restriction severing point as determined. In this way, the 3.7 kb XhoI-SalI-fragment, the 2.3 kb BamHI-fragment and the 7.2 kb BamHI fragment were ligated with the correspondingly severed and treated vector pJCl (Mol Gen. Genet.(1990)220: 478–480). With the ligation products *C. glutamicum* NA8 was directly transformed, the transformants were tested for having the lysine excretion properties and the presence of the subclone was confirmed by plasmid preparation and restriction analysis. In this way, the strain with plasmid pMV2-3 (FIG. 1) was obtained as smallest subclone. This fragment resulting in lysine export contains as insert the 2.3 kb Bam fragment from pMV6-3.

c) Sequence of the lysine export gene lys E and its regulators lysG.

The nucleotide sequence of the 2.3 kb BamH1 fragment was performed according to the dideoxy-chain termination method of Sanger et al. (Proc. Natl. Acad. Sci USA(1977) 74:5463-5467) and the sequencing reaction with the Auto Read Sequencing kit from Pharamcia (Uppsala, Sweden). The electrophoretic analysis occurs with the automatic laser-fluorescence DNA sequencing apparatus (A.L.F) from Pharmacia-LKB(Piscataway, N.J., USA). The nucleotide sequence obtained was analyzed by the program packet HUSAR (Release 3.0) of the German Cancer Research Center (Heidelberg). The nucleotide sequence and the result of the analysis is presented in SEQ ID No 1 and FIG. 2. The analysis results in two fully open reading frames (ORF) on the sequenced DNA piece. ORF1 codes for a protein with a length of 236 amino acids, OFR2 codes for a protein with a length of 290 amino acids. The protein derived from ORF1 includes an accumulation of hydrophobic amino acids as they are characteristic for membrane-embedded proteins. The detailed analysis of the distribution of the hydrophobic and hydrophilic amino acids by the programs PHD.HTM (Protein Science(1995)4:521–533) is shown in table 3. It is apparent therefrom that the protein contains six hydrophobic helix areas which extend through the membrane. Consequently, this protein is the searched for exporter of the amino acid L-lysine. The corresponding gene will therefore be designated below as lysE. In table 2, it is marked accordingly. ORF2 is transcribed in a direction opposite to ORF1. The sequence analysis shows that ORF2 has a high identity with regulator genes which are combined as a single family (Ann Rev Microbiol(1993) 597–626). Genes of this family regulate the expression processes of the various genes involved in catabolic or anabolic processes in a positive way. For this reason, ORF2 will below be designated as lysG (Govern=regulating). Because of the coordination and because IysE could be cloned (see a)) and subcloned (see b)) together with lysG, lysG is regulator of lysE and consequently also participates in the lysine export. The gene lysG and the amino acid sequence derived therefrom are also shown in SEQ ID No(B)1 and table 2 and, respectively, SEQ ID No.3.

d) Identification of an unknown membrane protein from *Escherichia coli* by sequence comparison.

With the established sequences according to table 3 already existing sequence banks can be searched in order to assign the proteins derived in this way from sequenced areas a certain function. Correspondingly, the amino acid sequence of the lysine exporters consisting of *C. glutamicum* were compared with derivated protein sequences of all the DNA sequences deposited there utilizing the program packet HUSAR (Release 3.0) of the German Cancer Research Center (Heidelberg). A high homology of 39.3% identical amino acids and 64.9% similar amino acids was found to a single sequence of so far unknown function of *E. coli*.

Figure 2:
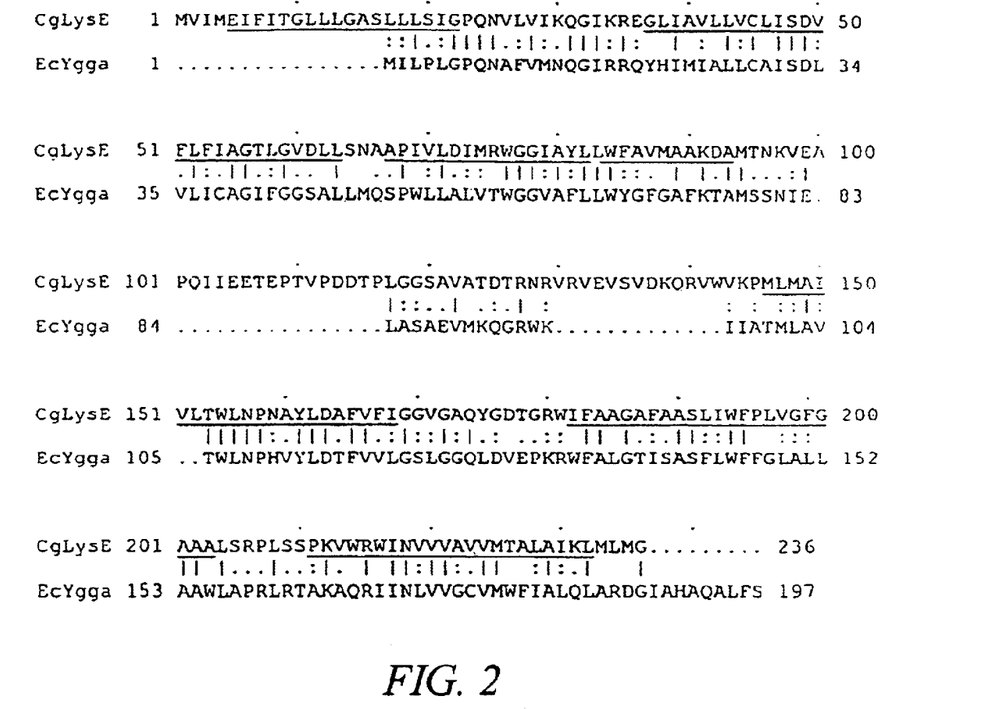
FIG. 2 shows a comparison of the derivated amino acid sequence of LysE from *C. glutamicum* (above), with a gene product of so far unknown function from *Escherichi coli* (below), which is identified thereby as export carrier.

The comparison is shown in FIG. 2. The open read frame of *E. coli* so far not characterized is consequently identified by way of this process as an amino export gene.

e) Increased export of intracellularly accumulated L-lysine.

Figure 3A:
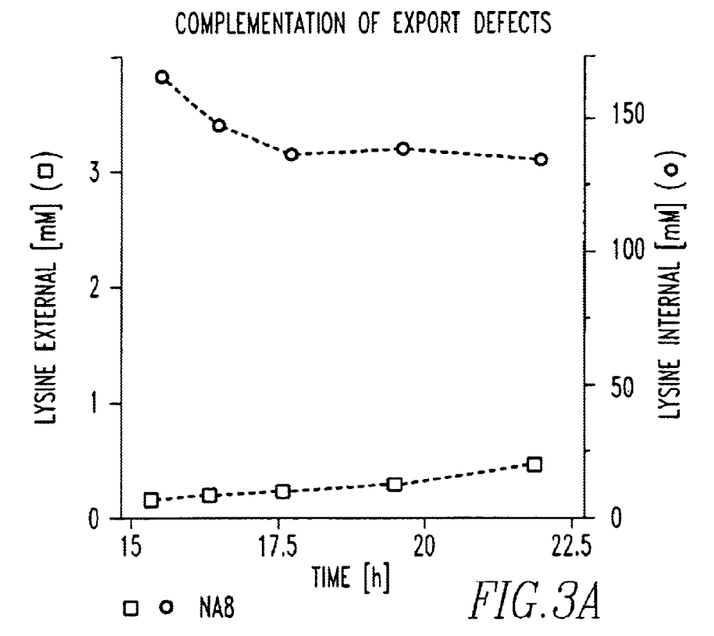
FIG. 3 shows increased lysine export by pMV2-3 with *C. glutamicum* NA8. On top, the control with low excretion and cellinternal backup of lysine up to about 150 mM. Below, the high secretion caused by pMV2-3 with cell internally only small backup of about 30 mM.
Figure 3B:
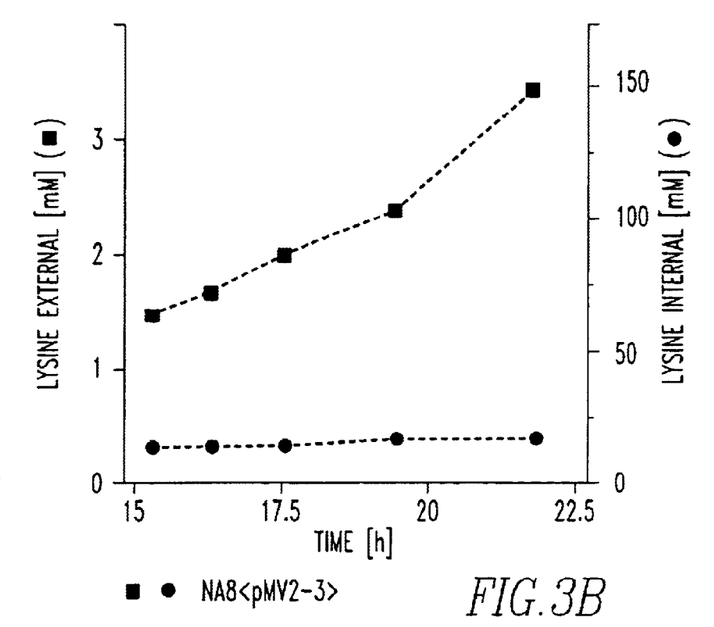

The strain *C. glutamicum* NA8 (J. Bacteriol(1995) 177: 4021–4027 was transformed with plasmid pMV2-3 and the L-lysine excretion of the strains was compared. For this purpose, NA8 and NA8pMV2-3 in complex medium were utilized as described in Vrljic et al. (J. Bacteriol (1995) 177:4021–40277) and the fermentation medium CGXII (Bacteriol (1993)175:5595–5603 were each separately inoculated. The medium additionally contained 5rnM L-methionin in order to induce the intracellular L-lysine biosynthesis. After cultivation for 24 hours at 30° C. on a rotary vibrator at 140 rpm, the cell internal and external L-lysine determinations were performed. For the cell-internal determination silicon oil centri-fugations were performed (Methods Enzymology LV(1979) 547–567); the determination of the amino acids occurred by high pressure liquid chromatography (J. Chromat (1983) 266:471–482). These de. terminations were performed at different times as indicated in FIG. 3. In accordance with the process used the retained cell internal L-lysine is excreted also by pMV2-3 to a greater degree and is accumulated. Accordingly, also the cell internally present L-lysine is greatly reduced. Consequently, the utilization of the newly discovered and described exporter represents a process for greatly improving the L-lysine production.

f) Increased accumulation of L-lysine by lysE or LysEG.

Figure 4:
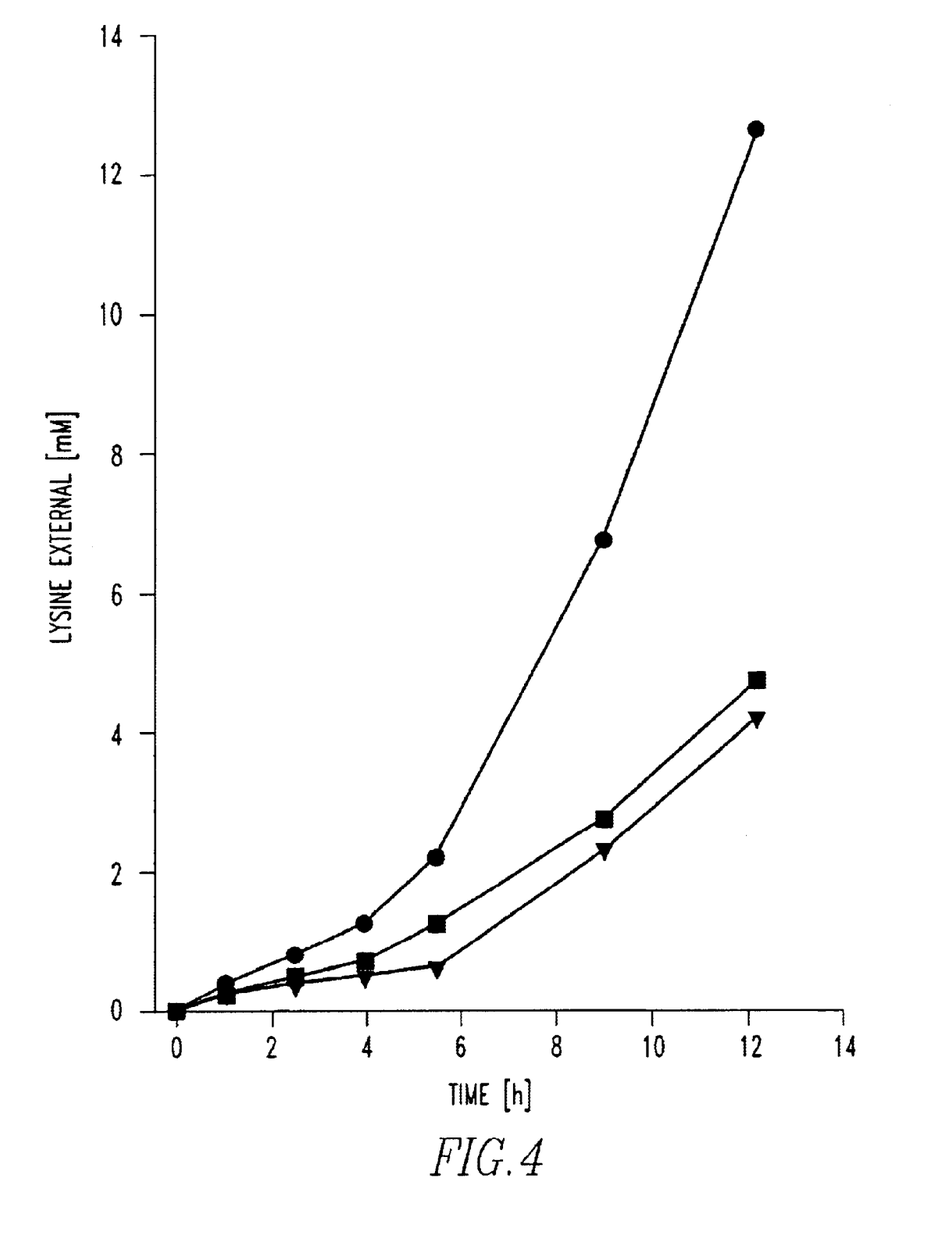
FIG. 4 shows the increase of the lysine accumulation in *C. glutamicum* by lys E lys G(pMV2-3) (middle curve), and the accumulation caused by lysE(plysE) (upper curve).

From the subclone pMV2-3 which contains the sequenced 2374 bp Bam HI-fragment in pJCI (see FIG. 1), the lysE carrying 1173 bpPvuII fragment was ligated in pZ1 (Appl. Env. Microbiol (1989)55:684–688) according to the sequence information and in this way, the plasmid plysE was obtained. This plasmid as well as the lysE lysG carrying plasmid pMV2-3 was introduced into *C. glutamicum* strained by electroporation wherein the chromosomal areas were deleted. The obtained strains *C. glutamicum* d pMV2-3, *C. glutamicum* d plysE, *C. glutamicum* pJCl were, as described under e) precultivated on a complex medium, then cultivated in production minimal medium CGx11 together with 4% glucose and 5 mM 1-methionin and samples were taken to determine the accumulated lysine. As apparent from FIG. 4 with lysE lysG an increase of the lysine accumulation with respect to a control sample is achieved. With plysE an extraordinarily increased accumulation of from 4.8 to 13.2 mM L-lysine is achieved with this method.

LEGENDS OF THE TABLES

Table 1: The amino acid sequence of the lysine exporter regulator from Corynebacterium glutamicum with the helix-turn-helix motive typical for DNA-binding proteins.

Table 2(three pages): The nucleotide sequence of *C. glutamicum* coding for the lysine exporter and lysine export regulators.

Table 3: the amino acid sequence of the lysine exporter from *Corynebacterium glutamicum* with the identified transmembrane helices TMH1 to TMH6.

Sequence Protocol A:

SEQ ID No. 1: Nucleotide sequence of the coding DNA strand and the amino acid sequence of the Lysine-exporter LysE derived therefrom.

SEQ ID No. 2: Amino acid sequence of the Lysine-exporter LysE.

Sequence Protocol B:

SEQ ID No.(B)1: Nucleotide sequence of the anti-sense strand and

Amino acid sequences of the Lysine-exporter-regulator LysG, derived therefrom and a ORF3.

SEQ ID No.(B)2: Amino acid sequence of the open reading frame (partial) ORF3.

SEQ ID No. 3: Amino acid sequence of the Lysine exporter-Regulator LysG.

What is claimed is:

1. A process for the microbacterial production of amino acids, comprising the steps of:
   1) providing a microbial organism having amino acid export carrier activity and having export gene-expression,
   2) increasing one of the export carrier activities of said microbial organism, wherein said export carrier has the amino acid sequence SEQ ID NO: 2, and the export carrier activity is endogenous to said microbial organism, and
   3) increasing the export gene expression of said export carrier, wherein said gene comprising nucleotides 1016 to 1726 of SEQ ID NO: 1 by means of one of the steps selected from the group of:

i) increasing the number of gene copies of the export carrier gene, ii) modifying regulatory signals assigned to the export carrier gene, and iii) amplifying regulatory signals assigned to the export carrier gene, whereby amino acids are produced by said microbial organism with increased efficiency, and 4) recovering the amino acids from the culture.

2. The process according to claim 1, wherein the export carrier gene expression of the export carrier is increased by increasing the number of gene copies, whereby the export carrier gene is expressed from the additional gene copies.

3. The process according to claim 2, wherein, in order to increase the number of export carrier gene copies, the export gene is inserted into a gene construct.

4. The process according to claim 3, wherein the export carrier gene is inserted into a vector with a low number copies.

5. The process according to claim 3, wherein the export carrier gene is inserted into a gene construct, which includes regulatory gene sequences operably linked to the export carrier gene.

6. The process according to claim 5, wherein the regulatory gene sequence includes a nucleotide sequence 1421–2293, coding for the amino acid sequence as given in SEQ ID NO: 3.

7. The process according to claim 3, wherein the microorganism producing the respective amino acid is transformed with the gene construct.

8. The process according to claim 7, wherein the microorganism is the type *Corynebacterium*.

9. The process according to claim 7, wherein, for the transformation, a microorganism is utilized in which the enzymes which participate in the synthesis of the corresponding amino acids are deregulated.

10. The process according to claim 7, wherein, for the transformation, a microorganism is utilized, which contains an increased amount of the metabolites of the central metabolism.

11. The process according to claim 2, wherein the export gene is isolated from a microorganism strain of the type *Corynebacterium*.

12. The process according to claim 1, wherein the export gene expression is increased by amplifying the transcription signals.

13. The process according to claim 1 for the manufacture of L-lysine.

14. A process for the increased microbial production of amino acids using an export carrier gene, comprising the steps of:

i) constructing a gene construct including an export carrier gene, ii) inserting said construct into a suitable vector, iii) transforming a suitable host cell with said vector, iv) cultivating said transformed host cell in a culture medium, v) recovering the amino acid(s) from the culture, and vi) determining the desired amino acid(s) amount.

15. The process according to claim 14, wherein the gene construct additionally carries regulatory gene sequences.

16. The process according to claim 14, wherein an export carrier gene from *Corynebacteriumn* is utilized.

17. The process according to claim 14, wherein *Corynebacterium* is used as amino acid producing microorganism.

* * * * *

SEQUENCE LISTING

<160> NUMBER OF SEQ ID NOS: 5

<210> SEQ ID NO 1
<211> LENGTH: 2374
<212> TYPE: DNA
<213> ORGANISM: Corynebacterium glutamicum
<220> FEATURE:
<221> NAME/KEY: gene
<222> LOCATION: CDS (1016)..(1726)
<223> OTHER INFORMATION: (LysE)

<400> SEQUENCE: 1
ccatttgctg aaggtgttac tctgcctggc ccaattcctg cgggcgaaga agtgaaaaac      60
cctgaacctt ttcagaagta actaaggccg caatccctcg attgctgcat caacgacggc     120
gtctgtgagt ctagctagag atctagattc caggcgccat cgttgccaat acatcggtgt     180

-continued

```
gtcaatgggt atctcatcga ggaggatcac ttctcctgct tttagcatgg gagcagcttg    240
ggtttcggga agaagtcccc aaccaaggcc tcggcgaatt gcctcaccaa aaccttccgc    300
cgacgggaca atggatacgc gcctgcgccc acaggacca tcgacgcgcc cgtccaggtc    360
acggtcttga agcacatctt tgggaccgaa gcgtaagacg ggcatcgcag cccaatctag    420
tttcccatca accatgtagg catcccgcaa tgagggggtt gcaatggcca agtgcgcat    480 ggttccaagt tctactactt cacatcccgc cacgggatta gcttcacggg ttaccgctcc    540
taaaacatct ccacgccgca gcaaggataa tgtgtgcgct tcatcttcca agcgcagcgt    600
gagcgttgct ccaccccaag aagctacctc gttgaacacg ggaggaaacc atgtggatag    660
cgaatctgcg ttgatggcga tggttaacgg gatttcagca aggcgtccag atagttgcgc    720
tttagtttct gcttgcagca acaccatttt ccgcgctgct gcacaagga cttcacccgc    780 ttcggttgct ttggccggtt gggtgcgcga taccaacact cgacccacgt gatgctcgag    840
agctttaacg cgctgactca ccgccgaggg ggaaatggaa agggctaagg aggcgccttc    900
gaagctgcct tcatcaatga ttgagagcaa agtgtccagt tgaatggggt tcatgaagct    960
atattaaacc atgttaagaa ccaatcattt tacttaagta cttccatagg tcacg atg   1018
                                                                    Met
                                                                     1 gtg atc atg gaa atc ttc att aca ggt ctg ctt ttg ggg gcc agt ctt    1066
Val Ile Met Glu Ile Phe Ile Thr Gly Leu Leu Leu Gly Ala Ser Leu
         5                  10                  15 tta ctg tcc atc gga ccg cag aat gta ctg gtg att aaa caa gga att    1114
Leu Leu Ser Ile Gly Pro Gln Asn Val Leu Val Ile Lys Gln Gly Ile
     20                  25                  30 aag cgc gaa gga ctc att gcg gtt ctc ctc gtg tgt tta att tct gac    1162
Lys Arg Glu Gly Leu Ile Ala Val Leu Leu Val Cys Leu Ile Ser Asp
 35                  40                  45 gtc ttt ttg ttc atc gcc ggc acc ttg ggc gtt gat ctt ttg tcc aat    1210
Val Phe Leu Phe Ile Ala Gly Thr Leu Gly Val Asp Leu Leu Ser Asn
 50                  55                  60                  65 gcc gcg ccg atc gtg ctc gat att atg cgc tgg ggt ggc atc gct tac    1258
Ala Ala Pro Ile Val Leu Asp Ile Met Arg Trp Gly Gly Ile Ala Tyr
             70                  75                  80 ctg tta tgg ttt gcc gtc atg gca gca aaa gac gcc atg aca aac aag    1306
Leu Leu Trp Phe Ala Val Met Ala Ala Lys Asp Ala Met Thr Asn Lys
         85                  90                  95 gtg gaa gcg cca cag atc att gaa gaa aca gaa cca acc gtg ccc gat    1354
Val Glu Ala Pro Gln Ile Ile Glu Glu Thr Glu Pro Thr Val Pro Asp
    100                 105                 110 gac acg cct ttg ggc ggt tcg gcg gtg gcc act gac acg cgc aac cgg    1402
Asp Thr Pro Leu Gly Gly Ser Ala Val Ala Thr Asp Thr Arg Asn Arg
     115                 120                 125 gtg cgg gtg gag gtg agc gtc gat aag cag cgg gtt tgg gta aag ccc    1450
Val Arg Val Glu Val Ser Val Asp Lys Gln Arg Val Trp Val Lys Pro
130                 135                 140                 145 atg ttg atg gca atc gtg ctg acc tgg ttg aac ccg aat gcg tat ttg    1498
Met Leu Met Ala Ile Val Leu Thr Trp Leu Asn Pro Asn Ala Tyr Leu
                150                 155                 160 gac gcg ttt gtg ttt atc ggc ggc gtc ggc gcg caa tac ggc gac acc    1546
Asp Ala Phe Val Phe Ile Gly Gly Val Gly Ala Gln Tyr Gly Asp Thr
             165                 170                 175 gga cgg tgg att ttc gcc gct ggc gcg ttc gcg gca agc ctg atc tgg    1594
Gly Arg Trp Ile Phe Ala Ala Gly Ala Phe Ala Ala Ser Leu Ile Trp
        180                 185                 190
```

-continued

| | | | | | | | | | | | | | | | |
|---|---|---|---|---|---|---|---|---|---|---|---|---|---|---|---|
| ttc | ccg | ctg | gtg | ggt | ttc | ggc | gca | gca | gca | ttg | tca | cgc | ccg | ctg | tcc | 1642 |
| Phe | Pro | Leu | Val | Gly | Phe | Gly | Ala | Ala | Ala | Leu | Ser | Arg | Pro | Leu | Ser |
| | 195 | | | | 200 | | | | | 205 | | | | | |

| | | | | | | | | | | | | | | | |
|---|---|---|---|---|---|---|---|---|---|---|---|---|---|---|---|
| agc | ccc | aag | gtg | tgg | cgc | tgg | atc | aac | gtc | gtc | gtg | gca | gtt | gtg | atg | 1690 |
| Ser | Pro | Lys | Val | Trp | Arg | Trp | Ile | Asn | Val | Val | Val | Ala | Val | Val | Met |
| 210 | | | | | 215 | | | | | 220 | | | | | 225 |

| | | | | | | | | | | |
|---|---|---|---|---|---|---|---|---|---|---|
| acc | gca | ttg | gcc | atc | aaa | ctg | atg | ttg | atg | ggt | tag ttttcgcggg | 1736 |
| Thr | Ala | Leu | Ala | Ile | Lys | Leu | Met | Leu | Met | Gly |
| | | | | 230 | | | | | 235 | | ttttggaatc ggtggccttc gcccaaatgt tgatgccggc gtcgtgggaa atctcatcga 1796 tcgcctccaa ctcggcgtca gaaaactcca agttgttgag tgaatcaagg ctgttgtcca 1856 gctgctcaac tgacgaagca ccaatcaatg cactggtcac ggtatccgcg ccgtactctc 1916 cttgctcgcg cagcacccat gcaagcgcca tctgcgcaag tgactgcccg cgttcctggg 1976 cgatgtcatt gagcttgcgg accatatcaa tattgttcac gttcaacatg ccctcagaca 2036 gggacttacc ctggctggcg cgggaaccct ctggaattcc atcgagatat ttgtccgtga 2096 gcaggccctg cgcaagtggt gagaaagcaa tgacgccaag accattgttg cagctgact 2156 gcaacaagtt ctcaccgtca tcgcccggtt cctccaccca acgattaatg atggaatagc 2216 ttggctgatg aatcagaagc gggcagccct cctccgccat gaactcagcc gcctccgctg 2276 tgagctctgg accgtaggaa gaaatacccca cgtaaagagc ctttccagac gcaacaatgt 2336 cacgcaatgc gtacatggtt tcttccaaag gagtatct 2374

<210> SEQ ID NO 2
<211> LENGTH: 236
<212> TYPE: PRT
<213> ORGANISM: Corynebacterium glutamicum
<220> FEATURE:
<223> OTHER INFORMATION: (LysE)

<400> SEQUENCE: 2

Met Val Ile Met Glu Ile Phe Ile Thr Gly Leu Leu Leu Gly Ala Ser
  1               5                  10                  15

Leu Leu Leu Ser Ile Gly Pro Gln Asn Val Leu Val Ile Lys Gln Gly
                 20                  25                  30

Ile Lys Arg Glu Gly Leu Ile Ala Val Leu Leu Val Cys Leu Ile Ser
             35                  40                  45

Asp Val Phe Leu Phe Ile Ala Gly Thr Leu Gly Val Asp Leu Leu Ser
         50                  55                  60

Asn Ala Ala Pro Ile Val Leu Asp Ile Met Arg Trp Gly Gly Ile Ala
 65                  70                  75                  80

Tyr Leu Leu Trp Phe Ala Val Met Ala Ala Lys Asp Ala Met Thr Asn
                 85                  90                  95

Lys Val Glu Ala Pro Gln Ile Ile Glu Glu Thr Glu Pro Thr Val Pro
            100                 105                 110

Asp Asp Thr Pro Leu Gly Gly Ser Ala Val Ala Thr Asp Thr Arg Asn
            115                 120                 125

Arg Val Arg Val Glu Val Ser Val Asp Lys Gln Arg Val Trp Val Lys
        130                 135                 140

Pro Met Leu Met Ala Ile Val Leu Thr Trp Leu Asn Pro Asn Ala Tyr
145                 150                 155                 160

Leu Asp Ala Phe Val Phe Ile Gly Val Gly Ala Gln Tyr Gly Asp
                165                 170                 175

Thr Gly Arg Trp Ile Phe Ala Ala Gly Ala Phe Ala Ala Ser Leu Ile
            180                 185                 190

```
Trp Phe Pro Leu Val Gly Phe Gly Ala Ala Leu Ser Arg Pro Leu
        195                 200                 205

Ser Ser Pro Lys Val Trp Arg Trp Ile Asn Val Val Ala Val Val
    210                 215                 220

Met Thr Ala Leu Ala Ile Lys Leu Met Leu Met Gly
225                 230                 235

<210> SEQ ID NO 3
<211> LENGTH: 2374
<212> TYPE: DNA
<213> ORGANISM: Corynebacterium glutamicum
<220> FEATURE:
<221> NAME/KEY: unsure
<222> LOCATION: CDS (2)..(652)
<223> OTHER INFORMATION: orf3
      (complement to SEQ ID No. 1)
<220> FEATURE:
<221> NAME/KEY: gene
<222> LOCATION: CDS (1421)..(2293)
<223> OTHER INFORMATION: LysG

<400> SEQUENCE: 3 a gat act cct ttg gaa gaa acc atg tac gca ttg cgt gac att gtt gcg        49
  Asp Thr Pro Leu Glu Glu Thr Met Tyr Ala Leu Arg Asp Ile Val Ala
   1               5                  10                  15 tct gga aag gct ctt tac gtg ggt att tct tcc tac ggt cca gag ctc         97
Ser Gly Lys Ala Leu Tyr Val Gly Ile Ser Ser Tyr Gly Pro Glu Leu
                 20                  25                  30 aca gcg gag gcg gct gag ttc atg gcg gag gag ggc tgc ccg ctt ctg        145
Thr Ala Glu Ala Ala Glu Phe Met Ala Glu Glu Gly Cys Pro Leu Leu
             35                  40                  45 att cat cag cca agc tat tcc atc att aat cgt tgg gtg gag gaa ccg        193
Ile His Gln Pro Ser Tyr Ser Ile Ile Asn Arg Trp Val Glu Glu Pro
         50                  55                  60 ggc gat gac ggt gag aac ttg ttg cag tca gct gcc aac aat ggt ctt        241
Gly Asp Asp Gly Glu Asn Leu Leu Gln Ser Ala Ala Asn Asn Gly Leu
 65                  70                  75                  80 ggc gtc att gct ttc tca cca ctt gcg cag ggc ctg ctc acg gac aaa        289
Gly Val Ile Ala Phe Ser Pro Leu Ala Gln Gly Leu Leu Thr Asp Lys
                 85                  90                  95 tat ctc gat gga att cca gag ggt tcc cgc gcc agc cag ggt aag tcc        337
Tyr Leu Asp Gly Ile Pro Glu Gly Ser Arg Ala Ser Gln Gly Lys Ser
            100                 105                 110 ctg tct gag ggc atg ttg aac gtg aac aat att gat atg gtc cgc aag        385
Leu Ser Glu Gly Met Leu Asn Val Asn Asn Ile Asp Met Val Arg Lys
        115                 120                 125 ctc aat gac atc gcc cag gaa cgc ggg cag tca ctt gcg cag atg gcg        433
Leu Asn Asp Ile Ala Gln Glu Arg Gly Gln Ser Leu Ala Gln Met Ala
    130                 135                 140 ctt gca tgg gtg ctg cgc gag caa gga gag tac ggc gcg gat acc gtg        481
Leu Ala Trp Val Leu Arg Glu Gln Gly Glu Tyr Gly Ala Asp Thr Val
145                 150                 155                 160 acc agt gca ttg att ggt gct tcg tca gtt gag cag ctg gac aac agc        529
Thr Ser Ala Leu Ile Gly Ala Ser Ser Val Glu Gln Leu Asp Asn Ser
                165                 170                 175 ctt gat tca ctc aac aac ttg gag ttt tct gac gcc gag ttg gag gcg        577
Leu Asp Ser Leu Asn Asn Leu Glu Phe Ser Asp Ala Glu Leu Glu Ala
            180                 185                 190 atc gat gag att tcc cac gac gcc ggc atc aac att tgg gcg aag gcc        625
Ile Asp Glu Ile Ser His Asp Ala Gly Ile Asn Ile Trp Ala Lys Ala
        195                 200                 205
```

-continued

| | |
|---|---|
| acc gat tcc aaa acc cgc gaa aac taa cccatcaaca tcagtttgat<br>Thr Asp Ser Lys Thr Arg Glu Asn<br>    210             215 | 672 |
| ggccaatgcg gtcatcacaa ctgccacgac gacgttgatc cagcgccaca ccttggggct | 732 |
| ggacagcggg cgtgacaatg ctgctgcgcc gaaacccacc agcgggaacc agatcaggct | 792 |
| tgccgcgaac gcgccagcgg cgaaaatcca ccgtccggtg tcgccgtatt gcgcgccgac | 852 |
| gccgccgata aacacaaacg cgtccaaata cgcattcggg ttcaaccagg tcagcacgat | 912 |
| tgccatcaac atgggcttta cccaaacccg ctgcttatcg acgctcacct ccacccgcac | 972 |
| ccggttgcgc gtgtcagtgg ccaccgccga accgccaaa ggcgtgtcat cgggcacggt | 1032 |
| tggttctgtt tcttcaatga tctgtggcgc ttccaccttg tttgtcatgg cgtctttcgc | 1092 |
| tgccatgacg gcaaaccata acaggtaagc gatgccaccc cagcgcataa tatcgagcac | 1152 |
| gatcggcgcg gcattggaca aaagatcaac gcccaaggtg ccggcgatga acaaaaagac | 1212 |
| gtcagaaatt aaacacacga gaagaaccgc aatgagtcct tcgcgcttaa ttccttgttt | 1272 |
| aatcaccagt acattctgcg gtccgatgga cagtaaaaga ctggccccca aaagcagacc | 1332 |
| tgtaatgaag atttccatga tcaccatcgt gacctatgga agtacttaag taaaatgatt | 1392 |
| ggttcttaac atggtttaat atagcttc atg aac ccc att caa ctg gac act<br>                              Met Asn Pro Ile Gln Leu Asp Thr<br>                                  220                 225 | 1444 |
| ttg ctc tca atc att gat gaa ggc agc ttc gaa ggc gcc tcc tta gcc<br>Leu Leu Ser Ile Ile Asp Glu Gly Ser Phe Glu Gly Ala Ser Leu Ala<br>            230                 235                 240 | 1492 |
| ctt tcc att tcc ccc tcg gcg gtg agt cag cgc gtt aaa gct ctc gag<br>Leu Ser Ile Ser Pro Ser Ala Val Ser Gln Arg Val Lys Ala Leu Glu<br>        245                 250                 255 | 1540 |
| cat cac gtg ggt cga gtg ttg gta tcg cgc acc caa ccg gcc aaa gca<br>His His Val Gly Arg Val Leu Val Ser Arg Thr Gln Pro Ala Lys Ala<br>    260                 265                 270 | 1588 |
| acc gaa gcg ggt gaa gtc ctt gtg caa gca gcg cgg aaa atg gtg ttg<br>Thr Glu Ala Gly Glu Val Leu Val Gln Ala Ala Arg Lys Met Val Leu<br>275                 280                 285 | 1636 |
| ctg caa gca gaa act aaa gcg caa cta tct gga cgc ctt gct gaa atc<br>Leu Gln Ala Glu Thr Lys Ala Gln Leu Ser Gly Arg Leu Ala Glu Ile<br>290                 295                 300                 305 | 1684 |
| ccg tta acc atc gcc atc aac gca gat tcg cta tcc aca tgg ttt cct<br>Pro Leu Thr Ile Ala Ile Asn Ala Asp Ser Leu Ser Thr Trp Phe Pro<br>            310                 315                 320 | 1732 |
| ccc gtg ttc aac gag gta gct tct tgg ggt gga gca acg ctc acg ctg<br>Pro Val Phe Asn Glu Val Ala Ser Trp Gly Gly Ala Thr Leu Thr Leu<br>        325                 330                 335 | 1780 |
| cgc ttg gaa gat gaa gcg cac aca tta tcc ttg ctg cgg cgt gga gat<br>Arg Leu Glu Asp Glu Ala His Thr Leu Ser Leu Leu Arg Arg Gly Asp<br>    340                 345                 350 | 1828 |
| gtt tta gga gcg gta acc cgt gaa gct aat ccc gtg gcg gga tgt gaa<br>Val Leu Gly Ala Val Thr Arg Glu Ala Asn Pro Val Ala Gly Cys Glu<br>355                 360                 365 | 1876 |
| gta gta gaa ctt gga acc atg cgc cac ttg gcc att gca acc ccc tca<br>Val Val Glu Leu Gly Thr Met Arg His Leu Ala Ile Ala Thr Pro Ser<br>370                 375                 380                 385 | 1924 |
| ttg cgg gat gcc tac atg gtt gat ggg aaa cta gat tgg gct gcg atg<br>Leu Arg Asp Ala Tyr Met Val Asp Gly Lys Leu Asp Trp Ala Ala Met<br>            390                 395                 400 | 1972 |
| ccc gtc tta cgc ttc ggt ccc aaa gat gtg ctt caa gac cgt gac ctg<br>Pro Val Leu Arg Phe Gly Pro Lys Asp Val Leu Gln Asp Arg Asp Leu<br>        405                 410                 415 | 2020 |

```
gac ggg cgc gtc gat ggt cct gtg ggg cgc agg cgc gta tcc att gtc    2068
Asp Gly Arg Val Asp Gly Pro Val Gly Arg Arg Val Ser Ile Val
        420                 425                 430 ccg tcg gcg gaa ggt ttt ggt gag gca att cgc cga ggc ctt ggt tgg    2116
Pro Ser Ala Glu Gly Phe Gly Glu Ala Ile Arg Arg Gly Leu Gly Trp
435                 440                 445 gga ctt ctt ccc gaa acc caa gct gct ccc atg cta aaa gca gga gaa    2164
Gly Leu Leu Pro Glu Thr Gln Ala Ala Pro Met Leu Lys Ala Gly Glu
450                 455                 460                 465 gtg atc ctc ctc gat gag ata ccc att gac aca ccg atg tat tgg caa    2212
Val Ile Leu Leu Asp Glu Ile Pro Ile Asp Thr Pro Met Tyr Trp Gln
            470                 475                 480 cga tgg cgc ctg gaa tct aga tct cta gct aga ctc aca gac gcc gtc    2260
Arg Trp Arg Leu Glu Ser Arg Ser Leu Ala Arg Leu Thr Asp Ala Val
                485                 490                 495 gtt gat gca gca atc gag gga ttg cgg cct tag ttacttctga aaaggttcag  2313
Val Asp Ala Ala Ile Glu Gly Leu Arg Pro
            500                 505 ggttttcac ttcttcgccc gcaggaattg ggccaggcag agtaacacct tcagcaaatg   2373
g                                                                  2374

<210> SEQ ID NO 4
<211> LENGTH: 216
<212> TYPE: PRT
<213> ORGANISM: Corynebacterium glutamicum
<220> FEATURE:
<223> OTHER INFORMATION: (orf3)

<400> SEQUENCE: 4

Asp Thr Pro Leu Glu Glu Thr Met Tyr Ala Leu Arg Asp Ile Val Ala
1               5                   10                  15

Ser Gly Lys Ala Leu Tyr Val Gly Ile Ser Ser Tyr Gly Pro Glu Leu
            20                  25                  30

Thr Ala Glu Ala Ala Glu Phe Met Ala Glu Glu Gly Cys Pro Leu Leu
        35                  40                  45

Ile His Gln Pro Ser Tyr Ser Ile Ile Asn Arg Trp Val Glu Glu Pro
    50                  55                  60

Gly Asp Asp Gly Glu Asn Leu Leu Gln Ser Ala Ala Asn Asn Gly Leu
65                  70                  75                  80

Gly Val Ile Ala Phe Ser Pro Leu Ala Gln Gly Leu Leu Thr Asp Lys
                85                  90                  95

Tyr Leu Asp Gly Ile Pro Glu Gly Ser Arg Ala Ser Gln Gly Lys Ser
            100                 105                 110

Leu Ser Glu Gly Met Leu Asn Val Asn Ile Asp Met Val Arg Lys
        115                 120                 125

Leu Asn Asp Ile Ala Gln Glu Arg Gly Gln Ser Leu Ala Gln Met Ala
    130                 135                 140

Leu Ala Trp Val Leu Arg Glu Gln Gly Glu Tyr Gly Ala Asp Thr Val
145                 150                 155                 160

Thr Ser Ala Leu Ile Gly Ala Ser Ser Val Glu Gln Leu Asp Asn Ser
                165                 170                 175

Leu Asp Ser Leu Asn Asn Leu Glu Phe Ser Asp Ala Glu Leu Glu Ala
            180                 185                 190

Ile Asp Glu Ile Ser His Asp Ala Gly Ile Asn Ile Trp Ala Lys Ala
        195                 200                 205

Thr Asp Ser Lys Thr Arg Glu Asn
    210                 215
```

<210> SEQ ID NO 5
<211> LENGTH: 290
<212> TYPE: PRT
<213> ORGANISM: Corynebacterium glutamicum
<220> FEATURE:
<223> OTHER INFORMATION: (LysG)

<400> SEQUENCE: 5

```
Met Asn Pro Ile Gln Leu Asp Thr Leu Leu Ser Ile Ile Asp Glu Gly
  1               5                  10                  15

Ser Phe Glu Gly Ala Ser Leu Ala Leu Ser Ile Ser Pro Ser Ala Val
                 20                  25                  30

Ser Gln Arg Val Lys Ala Leu Glu His His Val Gly Arg Val Leu Val
             35                  40                  45

Ser Arg Thr Gln Pro Ala Lys Ala Thr Glu Ala Gly Glu Val Leu Val
         50                  55                  60

Gln Ala Ala Arg Lys Met Val Leu Leu Gln Ala Glu Thr Lys Ala Gln
 65                  70                  75                  80

Leu Ser Gly Arg Leu Ala Glu Ile Pro Leu Thr Ile Ala Ile Asn Ala
                 85                  90                  95

Asp Ser Leu Ser Thr Trp Phe Pro Pro Val Phe Asn Glu Val Ala Ser
                100                 105                 110

Trp Gly Gly Ala Thr Leu Thr Leu Arg Leu Glu Asp Glu Ala His Thr
            115                 120                 125

Leu Ser Leu Leu Arg Arg Gly Asp Val Leu Gly Ala Val Thr Arg Glu
130                 135                 140

Ala Asn Pro Val Ala Gly Cys Glu Val Val Glu Leu Gly Thr Met Arg
145                 150                 155                 160

His Leu Ala Ile Ala Thr Pro Ser Leu Arg Asp Ala Tyr Met Val Asp
                165                 170                 175

Gly Lys Leu Asp Trp Ala Ala Met Pro Val Leu Arg Phe Gly Pro Lys
            180                 185                 190

Asp Val Leu Gln Asp Arg Asp Leu Asp Gly Arg Val Asp Gly Pro Val
            195                 200                 205

Gly Arg Arg Arg Val Ser Ile Val Pro Ser Ala Glu Gly Phe Gly Glu
210                 215                 220

Ala Ile Arg Arg Gly Leu Gly Trp Gly Leu Leu Pro Glu Thr Gln Ala
225                 230                 235                 240

Ala Pro Met Leu Lys Ala Gly Glu Val Ile Leu Leu Asp Glu Ile Pro
                245                 250                 255

Ile Asp Thr Pro Met Tyr Trp Gln Arg Trp Arg Leu Glu Ser Arg Ser
            260                 265                 270

Leu Ala Arg Leu Thr Asp Ala Val Val Asp Ala Ala Ile Glu Gly Leu
            275                 280                 285

Arg Pro
290
```